United States Patent [19]
Voit et al.

[11] Patent Number: 6,022,999
[45] Date of Patent: Feb. 8, 2000

[54] PREPARATION OF 3-AMINOMETHYL-3,5,5-TRIMETHYLCYCLOHEXYLAMINE HAVING A CIS/TRANS ISOMER RATIO OF AT LEAST 70:30

[75] Inventors: Guido Voit, Freinsheim; Tom Witzel, Ludwigshafen; Boris Breitscheidel, Limburgerhof; Hermann Luyken, Ludwigshafen; Karl-Heinz Ross, Grünstadt; Peter Wahl, Ladenburg, all of Germany

[73] Assignee: BASF Aktiengesellschaft, Ludwigshafen, Germany

[21] Appl. No.: 09/207,623

[22] Filed: Dec. 9, 1998

[30] Foreign Application Priority Data

Dec. 18, 1997 [DE] Germany .............................. 197 56 400

[51] Int. Cl.⁷ .................................................. C07C 209/22
[52] U.S. Cl. ............................................ 564/448; 546/446
[58] Field of Search ........................................ 564/446, 448

[56] References Cited

U.S. PATENT DOCUMENTS

| | | |
|---|---|---|
| 4,429,157 | 1/1984 | Disteldorf et al. . |
| 5,371,292 | 12/1994 | Merger et al. . |
| 5,373,068 | 12/1994 | Piana et al. . |
| 5,504,254 | 4/1996 | Haas et al. . |
| 5,536,691 | 7/1996 | Breitscheidel . |
| 5,583,260 | 12/1996 | Haas et al. . |
| 5,696,048 | 12/1997 | Breitscheidel et al. . |
| 5,756,845 | 5/1998 | Voit et al. . |

FOREIGN PATENT DOCUMENTS

| | | |
|---|---|---|
| 42 119 | 12/1981 | European Pat. Off. . |
| 449 089 | 10/1991 | European Pat. Off. . |
| 659 733 | 6/1995 | European Pat. Off. . |
| 659 734 | 6/1995 | European Pat. Off. . |
| 729 937 | 9/1996 | European Pat. Off. . |
| 742 04554 | 11/1996 | European Pat. Off. . |
| 42 11 454 | 10/1993 | Germany . |
| 43 25 847 | 2/1995 | Germany . |

OTHER PUBLICATIONS

Studies in Surface, Sci. and Catalysis, vol. 51, New Solid Acids and Bases 1989 pp. 1–3.

*Primary Examiner*—Samuel Barts
*Attorney, Agent, or Firm*—Keil & Weinkauf

[57] ABSTRACT

A process for the preparation of 3-aminomethyl-3,5,5-trimethylcyclohexylamine having a cis/trans isomer ratio of at least 70:30 by a) imination of 3-cyano-3,5,5-trimethylcyclohexanone with ammonia in the presence of an imination catalyst at temperatures of from 20° to 150° C. and pressures of from 1.5 to 30 MPa to form 3-cyano-3,5,5-trimethylcyclo-hexanone imine followed by b) hydrogenation of the 3-cyano-3,5,5-trimethylcyclohexanone imine in the presence of ammonia over a catalyst containing copper and/or a Group VIII metal at a temperature of from 80° to 160° C. and under a pressure of from 5 to 30 MPa, wherein the catalytic hydrogenation of the 3-cyano-3,5,5-trimethylcyclohexanone imine is carried out in the presence of an acid used in an amount such as to give an acid number of from 0.1 to 2, based on 3-cyano-3,5,5-trimethylcyclohexanone used.

7 Claims, No Drawings

PREPARATION OF 3-AMINOMETHYL-3,5,5-TRIMETHYLCYCLOHEXYLAMINE HAVING A CIS/TRANS ISOMER RATIO OF AT LEAST 70:30

DESCRIPTION

The present invention relates to processes for the preparation of 3-aminomethyl-3,5,5-trimethylcyclohexylamine having a cis/trans isomer ratio of at least 70:30 by a) imination of 3-cyano-3,5,5-trimethylcyclohexanone with ammonia in the presence of an imination catalyst at temperatures ranging from 20° to 150° C. and pressures ranging from 1.5 to 30 MPa to form 3-cyano-3,5,5-trimethylcyclohexanone imine followed by b) hydrogenation of 3-cyano-3,5,5-trimethylcyclohexanone imine in the presence of ammonia offer catalysts containing copper and/or a Group VIII metal at temperatures ranging from 80° to 160° C. and pressures ranging from 5 to 30 MPa.

3-Aminomethyl-3,5,5-trimethylcyclohexylamine (isophoronediamine, IPDA) is an important intermediate for polyamides and epoxy resins and for the preparation of the corresponding sophorone diisocyanate (IPDI), which is used as a component of polyurethanes.

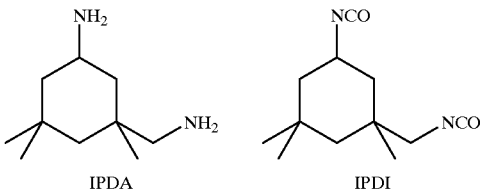

IPDA       IPDI

The IPDA molecule possesses two asymmetrically substituted carbon atoms and therefore exists in two diastereoisomeric forms, the cis isomer and the trans isomer, as illustrated by the scheme below.

In the preparation of IPDA from 3-cyano-3,5,5-trimethylcyclohexanone (isophorone nitrile, PN) by the steps comprising imination and subsequent hydrogenation in the presence of ammonia, the resulting cis/trans isomer ratio of the IPDA is not established until the hydrogenation step takes place (cf scheme below):

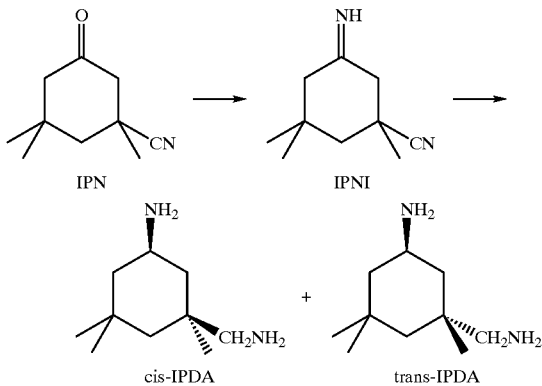

This isomer ratio is of very high industrial significance, since according to the teaching of DE-A 4,211,454 the two isomers show different reactivity properties when used as components of polyaddition resins, such as epoxy resins. For this reason, an IPDA having a content of cis isomers of 75% is therefore preferred in view of the reaction velocities attained and the properties of the product, and commercial IPDA (and consequently also the IPDI prepared therefrom) therefore possesses a cis/trans isomer ratio of 75:25.

EP-A 449,089 reveals a process for the preparation of IPDA from IPN. IPN is caused to react with ammonia in a first stage over acidic metal oxides acting as catalyst to produce 3-cyano-3,5,5-trimethylcyclohexanone imine (isophorone nitrile imine, IPNI) which is then hydrogenated in a second step following the addition of hydrogen in the presence of ammonia over known hydrogenating metals, preferably cobalt and/or ruthenium, to form the IPDA.

The process described in EP-A 449,089 makes it possible to prepare IPDA from IPN showing, compared with the aforementioned processes, a high space-time yield and a high chemical yield. Thus when use is made of aluminum oxide or titanium dioxide for imination and of highly active cobalt catalysts for hydrogenation, as described in, say, DE-A 4,325,847, yields of IPDA of 98% can be attained. The cis IPDA concentration in the effluent is, however, only from 60 to 66%.

EP-A 729,937 (page 3, Comparative Example A from EP-A 449,098) further discloses that the addition of NaOH to a single-stage hydrogenation process carried out over a cobalt catalyst causes the yield of IPDA to be increased from 92% to 97%, but also results in a drop in the isomer ratio from 68:32 to 60:40.

EP-A 659,734 reveals that it is possible to prepare IPDA having a cis/trans isomer ratio above that obtained when use is made of a cobalt catalyst when aminating hydrogenation of IPN is carried out in trickle bed reactors in the presence of a ruthenium catalyst and, optionally, a downstream cobalt catalyst (loc. cit. pp 5, lines 36–40).

A drawback of this process however, is that it provides poor yields of IPDA of only 82 to 87% (loc. cit. Examples 9 to 11).

In order to achieve cis/trans isomer ratios of at least 70:30 in effluents from syntheses of IPDA starting from IPN, two other industrial processes have been postulated, the teaching of which substantially consists in carrying out the hydrogenation stage in two steps at different temperatures:

EP-A 729,937 describes the preparation of IPDA from IPN to give yields of ≧96% containing a higher cis isomer concentration (>67% ), by carrying by carrying out the following steps in three discrete reaction chambers:

a) reaction of the IPN with $NH_3$ over acidic metal oxide catalysts (=imination catalyst) at temperatures ranging from 20° to 150° C. and pressures ranging from 5 to 30 MPa, b) hydrogenation of the resulting reaction products in a second reaction chamber using hydrogen in the presence of $NH_3$ over hydrogenating catalysts at temperatures ranging from 50° to 100° C. and pressures ranging from 5 to 30 MPa and c) hydrogenation of the resulting reaction products in a third reaction chamber in the presence of hydrogen and $NH_3$ over hydrogenating catalysts at temperatures ranging from 110° to 160° C. and pressures ranging from 15 to 30 MPa.

A disadvantage of this process is the expenditure incurred due to the apparatus required by the two in-line hydrogenating pressure reactors.

EP-A 659,733 discloses a way of controlling the cis/trans isomer ratio in the preparation of IPDA by aminating hydrogenation of IPN in the presence of ammonia, $H_2$ and a hydrogenating catalyst by carrying out the reaction in two stages at different temperatures, namely first at from 10° to 90° C. and then at from 90° to 150° C., the temperature difference between the two stages being at least 30° C., while the period of contact in the first stage is shorter than in the second. Lowering the temperature in the first stage causes an increase in the cis/trans isomer ratio. According to the examples of EP-A 659,733, if use is made of a reaction temperature in the second reactor of 120° C. and of an at least 30° C. lower temperature in the first reactor, cis/trans isomer ratios of at least 70:30 can be achieved.

A disadvantage of this process is again the expenditure involved by apparatus made necessary by the two in-line hydrogenating pressure reactors.

It is thus an object of the invention to provide an alternative economical process for the preparation af IPDA, which process is simpler to engineer, gives high chemical yields and high space-time yields and also increases the content of cis IPDA.

Accordingly, we have found a novel and improved process for the preparation of IPDA having a cis/trans isomer ratio of at least 70:30 by a) imination of 3-cyano-3,5,5-trimethylcyclohexanone with ammonia in the presence of an imination catalyst at temperatures of from 20° to 150° C. and pressures of from 1.5 to 30 MPa to form 3-cyano-3,5,5-trimethylcyclohexanone imine followed by b) hydrogenation of the 3-cyano-3,5,5-trimethylcyclohexanone imine in the presence of ammonia over catalysts containing copper and/or a Group VIII metal at temperatures of from 80° to 160° C. and pressures of from 5 to 30 MPa, said process being characterized in that the catalytic hydrogenation of the 3-cyano-3,5,5-trimethylcyclohexanone imine is carried out in the presence of an acid which is present in an amount such as to give an acid number of from 0.1 to 2, based on IPN used.

The process of the invention may be carried out as follows:

Stage a)

In the first process stage, IPN is caused to react with excess ammonia in the presence of an imination catalyst at temperatures of from 20° to 150° C., preferably from 30° to 130° C. and more preferably from 50° to 100° C., and pressures of from 1.5 to 30 MPa, preferably from 10 to 25 MPa, to form 3-cyano-3,5,5-trimethylcyclohexanone imine (IPM).

In this case an IPN is used which has either an acid number (AN) ranging from 0 to <0.1 or an AN in the range of from 0.1 to 2, preferably from 0.2 to 1.

The acid number (AN) specifies the number of milligrams of potassium hydroxide that are necessary for neutralisation of the free acids present in 1 g of substance (cf eg European Pharmacopeia, 3rd Edition, pp 67, Deutscher Apotheker Verlag Stuttgart-Govi Verlag-Pharmazeutischer Verlag, 1997). The AN is calculated as follows:

AN=5.610•n/m, where m is the initially weighed quantity of the substance in grams and n is the volume in mL of 0.1M potassium hydroxide solution required for titration.

Since it contains no acid groupings in the molecule, IPN possesses an AN equal to zero according to the above definition of the acid number.

The addition of appropriate amounts of acid to the IPN makes it possible to adjust the acid number to a value in the range of from 0.1 to 2. For example, if IPN is admixed with 0.129 g of 2-ethylhexanoic acid per 100 g, it is found to have an AN of 0.5 when titrated.

Suitable acids for use in the process of the invention are all acids which make it possible to adjust the AN of IPN to from 0.1 to 2 when added to IPN in appropriate amounts.

Suitable acids are Lewis acids and Broenstedt acids, preferably Broenstedt acids and mixtures thereof, more preferably Broenstedt acids having a pKs value below 150 and most preferably organic Broenstedt acids, such as monocarboxylic acids and dicarboxylic acids.

Examples of suitable acids are Lewis acids such as aluminum trichloride, zinc dichloride, boron trifluoride, boron trifluoride etherate, inorganic acids such as phosphoric acid, phosphorous acid and sulfuric acid, sulfonic acids such as methanesulfonic acid and p-toluenesulfonic acid, and $C_1$–$C_{20}$ carboxylic acids such as formic acid, acetic acid, methoxyacetic acid, propionic acid, capronic acid, lauric acid, benzoic acid, phthalic acid, phenylacetic acid, 2-ethylhexanoic acid, succinic acid, glutaric acid, adipic acid, suberic acid, sebacic acid, preferably acetic acid, 2-ethylhexanoic acid and adipic acid and more preferably 2-ethylhexanoic acid.

Suitable imination catalysts are for example solid Broenstedt or Lewis acids such as are described in EP-A 449,089 (pp 2, column 2, lines 10–18), in EP-A 42,119 and in "Studies in Surface Science and Catalysis", Vol. 51, pp 1 et seq (Elsevier, 1989): K. Tanabe et al, "New Solid Acids—their catalytic properties". As examples there may be mentioned here acidic metal oxide catalysts such as aluminum oxide, titanium dioxide and zirconium dioxide, or inorganic or organic ion exchangers charged with ammonium ions, such as zeolites or sulfonated copolymers of styrene and divinylbenzene (eg the brands Lewatit®, Amberlite®) or exchangers based on siloxane (eg the brand Deloxan®).

When use is made of acidic metal oxides or ion exchangers as imination catalysts, the space velocity is maintained at from 0.01 to 10, preferably from 0.05 to 7 and more preferably from 0.1 to 5, kg of IPN per kg of catalyst per hour.

It is convenient but not absolutely necessary to use, per mole of IPN, from 5 to 500 mol of $NH_3$, preferably from 10 to 400 mol of $NH_3$, and more preferably from 20 to 300 mol of $NH_3$, during imination.

The imination of the IPN can also be carried out in the presence of a solvent such as an alkanol or tetrahydrofuran, but we prefer to operate without the addition of a solvent.

The imination is preferably carried out continuously in, eg, pressure vessels or cascades of pressure vessels. In a particularly preferred embodiment IPN and $NH_3$ are passed through a tubular reactor in which imination catalyst is located in the form of a fixed bed.

Stage b)

If the imination stage (stage a) see above) has been carried out using an IPN which had an acid number of from 0.1 to 2, the reaction product that is obtained in stage a) is directly used in the subsequent stage b) (see below).

If stage a) has been carried out using an IPN possessing an acid number of 0 to <0.1, an acid is added to the effluent obtained in stage a) in an amount appropriate to give an acid number of from 0.1 to 2, preferably from 0.2 to 1, based on IPN used. As regards the type of useful and preferred acids the same applies here as stated above for the imination stage a). If stage b) is to be carried out continuously (see below), the acid can be continuously fed to the reactor.

The effluent obtained in the imination stage, which by reason of the aforementioned measures contains an acid in an amount corresponding to an acid number of from 0.1 to 2, preferably from 0.2 to 1, based on IPN used, is subjected, in a second stage, to catalytic hydrogenation using from 3 to 10,000 mole equivalents (based on isophorone nitrile imine) of hydrogen, preferably from 4.5 to 100 mole equivalents of $H_2$, optionally following the addition of more ammonia.

The hydrogenation takes place at reaction temperatures of from 80° to 160° C., for example at 100°, 120°, 130°, 140° or 150° C., preferably at from 120° to 150° C., and a pressure of from 5 to 30 Mpa, preferably from 10 to 25 MPa.

Suitable hydrogenating catalysts are basically all hydrogenating catalysts containing nickel, cobalt, iron, copper, ruthenium and/or other Group VIIIB metals. We prefer to use catalysts containing ruthenium and/or cobalt and/or nickel. We particularly prefer ruthenium and cobalt catalysts and mixtures thereof. The catalytically active metals can be used as solid catalysts or supported catalysts. Suitable supports are eg aluminum oxide, titanium dioxide, zirconium dioxide, zinc oxide or magnesium oxide/aluminum oxide, whilst supports containing basic components such as oxides and hydroxides of alkali metals and alkaline earth metals are preferred. Particularly preferred are solid catalysts, such as are disclosed in DE-A 4,325,847 and EP-A 742,045, which contain basic components such as oxides or hydroxides of alkali metals and alkaline earth metals.

The space velocities used when the process is carried out continuously (given in kg of feed/[kg of catalyst•hour]) advantageously range from 0.01 to 5 kg/[kg•h], preferably from 0.02 to 2.5 kg/[kg•h] and more preferably from 0.05 to 2 kg/[kg•h].

The hydrogenation is preferably carried out in liquid ammonia. Per mole of 3-cyano-3,5,5-trimethylcyclohexanone imine (IPNI) there are used from 5 to 500 mol, preferably from 10 to 400 mol and more preferably from 20 to 300 mol, of $NH_3$. It is advantageous to use at least that rate of $NH_3$ which was used in the previous preparation of IPNI from IPN (stage a). However, the $NH_3$ concentration may be raised to the desired value prior to hydrogenation by the addition of more $NH_3$.

The hydrogenation of 3-cyano-3,5,5-trimethylcyclohexanone imine (IPNI) in the presence of $NH_3$ is preferably carried out continuously in, say, pressure-tight stirred vessels or in a cascade of stirred vessels. In a particularly preferred embodiment, tubular reactors are used in which the hydrogenation takes place in upward or downward flow mode over a fixed catalyst bed.

If the effluent from the hydrogenation stage (stage b) still contains components that are not quantitatively converted, such as 3-cyano-3,5,5-trimethylcyclohexylamine ('aminonitrile'), which requires very elaborate means for isolation, by distillation, from the IPDA, it can be caused to react, in a third stage (stage c)), in the presence of hydrogen and ammonia., over the hydrogenating catalysts described for stage b) at reaction temperatures of from 110° to 160° C., for example 120°, 130°, 140° or 150° C., and pressures ranging from 5 to 30 MPa, preferably from 15 to 25 MPa. Advantageously, the ammonia and hydrogen feed used is the same as that resulting at the reactor outlet of stage b).

The reactor of stage c), which in a preferred embodiment is a tubular reactor containing a fixed catalyst bed, can be distinctly smaller than that used in stage b). For example, the reactor of stage c) can have a capacity which is equal to from 20 to 40% of the capacity of the reactor of stage b).

Following hydrogenation, excess ammonia and optionally hydrogen are separated from the effluent optionally under pressure. The crude IPDA thus obtained, having a cis/trans isomer ratio of at least 70:30, can be isolated as pure substance by fractional rectification.

EXAMPLE

Into two in-line tubular reactors, the first of which (the imination reactor) was packed with 400 mL of γ-aluminum oxide (4 mm extrudates) and the second (the hydrogenating reactor) with 800 mL of a cobalt catalyst (4 mm extrudates) having a cobalt content of 90%, such as is described in EP-A 742,045 (page 4), there were introduced 160 g/h of isophorone nitrile (IPN) having an acid number of <0.1 and 480 g/h of liquid $NH_3$. Upstream of the hydrogenating reactor there were additionally fed in 500 L(STP)/h of hydrogen. (L(STP)=standard liters=volume under standard conditions). The pressure in both reactors was 25 MPa, the reaction temperature being 85° C. in the first reactor and 135° C. in the second reactor.

Gas-chromatographic analysis of the effluent showed a cis/trans IPDA isomer ratio of 66:34.

Following an on-stream period of 1130 h, the IPN was adjusted to an acid number of 0.5 (g of KOH/kg of IPN) by the addition of an appropriate amount of 2-ethylhexanoic acid. Afterwards the cis/trans IPDA isomer ratio in the effluent rose to 75:25, and the yield of IPDA was 92%.

We claim:

1. A process for the preparation of 3-aminomethyl-3,5,5-trimethylcyclohexylamine having a cis/trans isomer ratio of at least 70:30 by
   a) imination of 3-cyano-3,5,5-trimethylcyclohexanone with ammonia in the presence of an imination catalyst at temperatures of from 20° to 150° C. and pressures of from 1.5 to 30 MPa to form 3-cyano-3,5,5-trimethylcyclohexanone imine followed by
   b) hydrogenation of the 3-cyano-3,5,5-trimethylcyclohexanone imine in the presence of ammonia over a catalyst containing copper and/or a Group VIII metal at a temperature of from 80° to 160° C. and under a pressure of from 5 to 30 MPa, wherein the catalytic hydrogenation of the 3-cyano-3,5,5-trimethylcyclohexanone imine is carried out in the presence of an acid used in an amount such as to give an acid number of from 0.1 to 2, based on 3-cyano-3,5,5-trimethylcyclohexanone used.

2. A process as defined in claim 1, wherein the catalytic hydrogenation of 3-cyano-3,5,5-trimethylcyclohexanone imine is carried out in the presence of an acid, the amount of which corresponds to an acid number of from 0.2 to 1 based on 3-cyano-5,5,5-trimethylcyclohexanone used.

3. A process as defined in claim 1, wherein the acid used is a Broenstedt acid or a mixture of Broenstedt acids.

4. A process as defined in claim 3, wherein the Broenstedt acid possesses a pKs-value of less than 6.

5. A process as defined in claim 3, wherein the acid used is an organic Broenstedt acid.

6. A process as defined in claim 5, wherein the acid used is a mono- or di-carboxylic acid or a mixture thereof.

7. A process as defined in claim 6, wherein the acid used is 2-ethylhexanoic acid.

* * * * *